United States Patent
Lean et al.

(10) Patent No.: US 8,852,446 B2
(45) Date of Patent: Oct. 7, 2014

(54) PLATELET EXTRACTION FROM BLOOD

(75) Inventors: Meng H. Lean, Santa Clara, CA (US); Armin R. Volkel, Mountain View, CA (US); Huangpin B. Hsieh, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 580 days.

(21) Appl. No.: 13/251,412

(22) Filed: Oct. 3, 2011

(65) Prior Publication Data

US 2013/0082012 A1    Apr. 4, 2013

(51) Int. Cl.
*B01D 21/26* (2006.01)
*B01D 21/02* (2006.01)
*A61M 1/00* (2006.01)

(52) U.S. Cl.
CPC .............. *B01D 21/02* (2013.01); *B01D 21/265* (2013.01); *A61M 1/0058* (2013.01)
USPC ............................ 210/804; 210/294; 210/295

(58) Field of Classification Search
CPC .... A61M 1/0058; B01D 21/02; B01D 21/265
USPC .......................................... 210/294, 295, 806
See application file for complete search history.

(56) References Cited

U.S. PATENT DOCUMENTS

| | | | |
|---|---|---|---|
| 6,398,972 B1 | 6/2002 | Blasetti et al. | |
| 6,716,187 B1 | 4/2004 | Jorgensen et al. | |
| 7,452,344 B2 | 11/2008 | Jorgensen et al. | |
| 2002/0104808 A1 | 8/2002 | Blasetti et al. | |
| 2005/0247564 A1 | 11/2005 | Volkel et al. | |
| 2006/0121555 A1 | 6/2006 | Lean et al. | |
| 2008/0128331 A1* | 6/2008 | Lean et al. | 209/155 |
| 2009/0283455 A1 | 11/2009 | Lean et al. | |

OTHER PUBLICATIONS

Kumar et al., "Electric Field-Driven Formation of Particle Concentration Fronts in Suspensions", Fluid Dynamics Researcy 39 (2007) pp. 169-192.
Spengler et al., "Microstreaming Effects on Particle Concentration in an Ultrasonic Standing Wave", AIChE Journal, Nov. 2003, vol. 49, No. 11, pp. 2773-2782.
Fabry, "Mechanism of Erythrocyte Aggregation and Sedimentation", Blood, vol. 70, No. 5, Nov. 1987, pp. 1572-1576.
McWhirter et al., "Flow-Induced Clustering and Alignment of Vesicles and Red Blood Cells in Microcapillaries", PNAS, Apr. 14, 2009, vol. 106, No. 15, pp. 6039-6043.

\* cited by examiner

*Primary Examiner* — Dirk Bass
(74) *Attorney, Agent, or Firm* — Fay Sharpe LLP (57) ABSTRACT

Systems and methods are used to concentrate and extract platelets from blood, where an aggregation arrangement is configured to aggregate red blood cells in the blood. The aggregated red blood cells are provided to a separation arrangement which is configured to separate the aggregated red blood cells from platelets in the blood plasma. Finally a concentration arrangement is configured to concentrate the platelets for extraction and further use.

17 Claims, 7 Drawing Sheets

PLATELET EXTRACTION FROM BLOOD

BACKGROUND

The present application is directed to the separation of components found in whole blood, and more particularly to the separation and extraction of platelets from other blood components such as red blood cells (erythrocytes) and white blood cells (leukocytes).

Platelets, while not considered real cells, are essential for certain biological operations such as blood clotting in a process called "hemostasis" (i.e. the stopping of bleeding) and are also a natural source of growth factors (which stimulate cell growth). Patients with certain diseases, such as AIDS and patients undergoing medical procedures including chemotherapy, bone marrow transplants, stem cell treatments, organ transplants and orthopedic procedures, among others often require regular and repeated transfusions of platelets.

For example, platelet-rich plasma (PRP) is often used in medical procedures where growth factors promote wound healing. One particularly interesting emerging application is in orthopedics, where patients who have undergone surgeries such as knee or hip replacements generally benefit from PRP obtained from whole blood. It is also considered beneficial to use platelets from a patient's own blood as this is understood to minimize immune response.

Collected whole blood is generally separated into components by one of three methods. A centrifuge can be used in a "soft spin" (~200×G) which separates whole blood into plasma (including platelets and white blood cells) and red blood cells or in a "hard spin" (greater than 200×G) which further separates the white blood cells from the platelets, in addition to the separation of the red blood cells. The third method is sedimentation where the blood simply sits for an extended period time until the red blood cells and plasma are separated by gravity. Still another described method of blood separation involves absorption of the blood component onto beads coated with an absorbent material. Wherein the coating is selected to absorb a particular type of component.

A well-known blood separation technique called aphaeresis employs centrifuge operations, and includes taking blood from a donor or patient, passing the blood through an apparatus that separates out desired components and returns the remainder of the blood to circulation. These centrifuge operations separate out the components based on component density. It is known that red-blood cells have the highest density, then white blood cells, and finally platelets. Therefore, depending on how many different components of the blood are needed, the blood will be subjected to various intervals of centrifugal steps, i.e., the "soft spin" and/or "hard spin". In addition, some devices use density gradient to help the separation and ensure separated layers stay apart. If enrichment (concentration) of platelets is desired, a porous barrier is further used to allow the passage of plasma but retains platelets. Most of these aphaeresis/platelet separation machines and other blood separation machines are generally bulky and often require a dedicated facility and operator which then requires a donor to visit the facility.

It is therefore considered beneficial to have a smaller, simpler device where blood can be drawn and the separation performed at the same location, without having to go through the procedure of being sent to a central lab, logged and placed in a queue for separation. Such a device could also potentially provide cost-savings, as longer single-use disposable tubing is employed to line large centrifuge based systems. Another advantage of a small portable separation device is minimal cross contamination, since different patients do not share the same instrument, just like disposable syringes.

BRIEF DESCRIPTION

Systems and methods are used to concentrate and extract platelets from blood, where an aggregation arrangement is configured to aggregate red blood cells in the blood. The aggregated red blood cells are provided to a separation arrangement which is configured to separate the aggregated red blood cells from platelets in the blood plasma. Finally a concentration arrangement is configured to concentrate the platelets for extraction and further use.

DETAILED DESCRIPTION

As described above a primary procedure for separating and extracting components from blood relies on the use of centrifugation. However, to implement blood separation using this and other existing techniques requires the use of complex, expensive, non-portable machines. On the other hand while sedimentation is another potential procedure the time needed to complete sedimentation is commonly not acceptable (e.g., from hours to overnight or longer). Therefore, described below are systems and methods which improve upon these existing processes and systems, by disclosure of concepts that may be implemented as less expensive, less complex, time appropriate, and if desired, portable devices.

Figure 1:
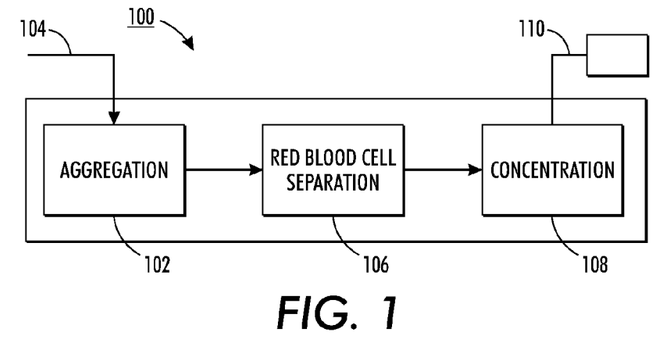
FIG. 1 illustrates a high level view of a blood separation device according to the concepts of the present application.
Figure 2:
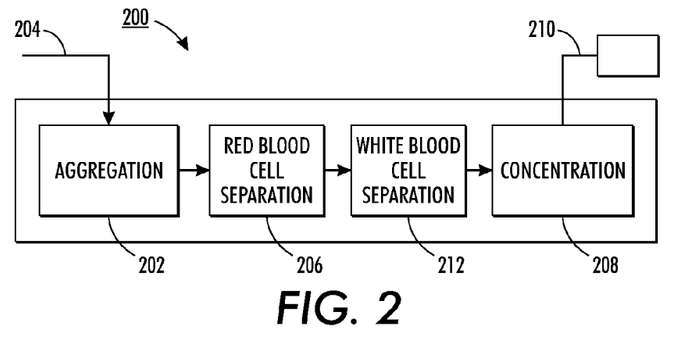
FIG. 2 illustrates a second embodiment of a high level for a blood separation device according to the concepts of the present application.

Turning now to FIGS. 1 and 2 illustrated are high level views of blood separation devices 100 and 200 according to the concepts of the present application. It is to be understood that additional details will be provided following this high level introduction.

Blood separation device 100 includes an aggregation stage or arrangement 102 configured to receive blood 104. In aggregation arrangement 102, the aggregation of red blood cells is initiated through the addition of a proper coagulant. A typical procedure for aggregating red blood cells is the addition of neutral or positively charged polymer, such as dextran, to the blood [see e.g.: T. L. Fabry, Blood, 70, 1572-1576, (1987), incorporated herein in its entirety]. The polymer molecules link the red blood cells into chains (rouleaux formation) that eventually collapse into dense aggregates. As will be expanded upon below, in an optional embodiment, a channel structure is provided through which the blood is passed in order to speed up rouleaux formation. Additional discussion regarding alignment of red blood cells in narrow channels (e.g., capillaries) is found in the paper by McWhirter et al., "Flow-Induced Clustering And Alignment Of Vesicles And Red Blood Cells In Microcapillaries", PNAS, 106, 6039-6043 (2009), incorporated herein in its entirety. However, it is understood that any other method that can initiate/induce the aggregation of red blood cells into larger conglomerates for sedimentation can be used with aggregation stage 102.

Blood 104 containing aligned-chained red blood cells is passed from aggregation arrangement 102 to a red blood cell separation stage or arrangement 106. Depending on the degree of aggregation achieved in the aggregation stage 102 the separation arrangement is designed to provide further aggregation of the red blood cells. This feature is especially useful when the blood is fed directly from the optional red blood cell alignment stage to the sedimentation stage. Following sufficient aggregation the red blood cells separate from other components (e.g., platelets and white blood cells carried in the blood plasma). Thereafter blood plasma, and the platelets and white blood cells suspended in it are supplied to a concentration stage or arrangement 108, where the platelets are further concentrated prior to being collected by a collection stage or arrangement 110 for further use.

It is understood the system described above does not act to separate white blood cells from the concentrated platelets. This is deemed acceptable due to the small number of white blood cells in blood compared to red blood cells. Also white blood cells are known to be robust and are unlikely to be damaged during the concentration and extraction of the platelets. Red blood cells on the other hand are known to be more fragile. Damage to the red blood cells, such as a breaking of the cells therefore carries a much greater risk of compromising the integrity of the platelets. It is nevertheless appreciated that in certain applications it may be desirable to also separate out the white blood cells from the platelets.

Therefore attention is now directed to blood separation device 200 of FIG. 2. Depicted is a device similar to that shown in FIG. 1, including a similar aggregation stage or arrangement 202 (which receives blood 204), a separation stage or arrangement 206, a concentration stage or arrangement 208, and a collection stage or arrangement 210. However, additionally provided is a white blood cell separation stage or arrangement 212. Thus, FIG. 2 provides the further capability of separating and optionally concentrating white blood cells in addition to platelets.

In one embodiment the present systems and methods employ sedimentation to separate components of the blood. An issue related to sedimentation is however the extended time needed for sedimentation to occur. Therefore an aspect of the present systems and methods is acceleration of the sedimentation process.

Figure 3:
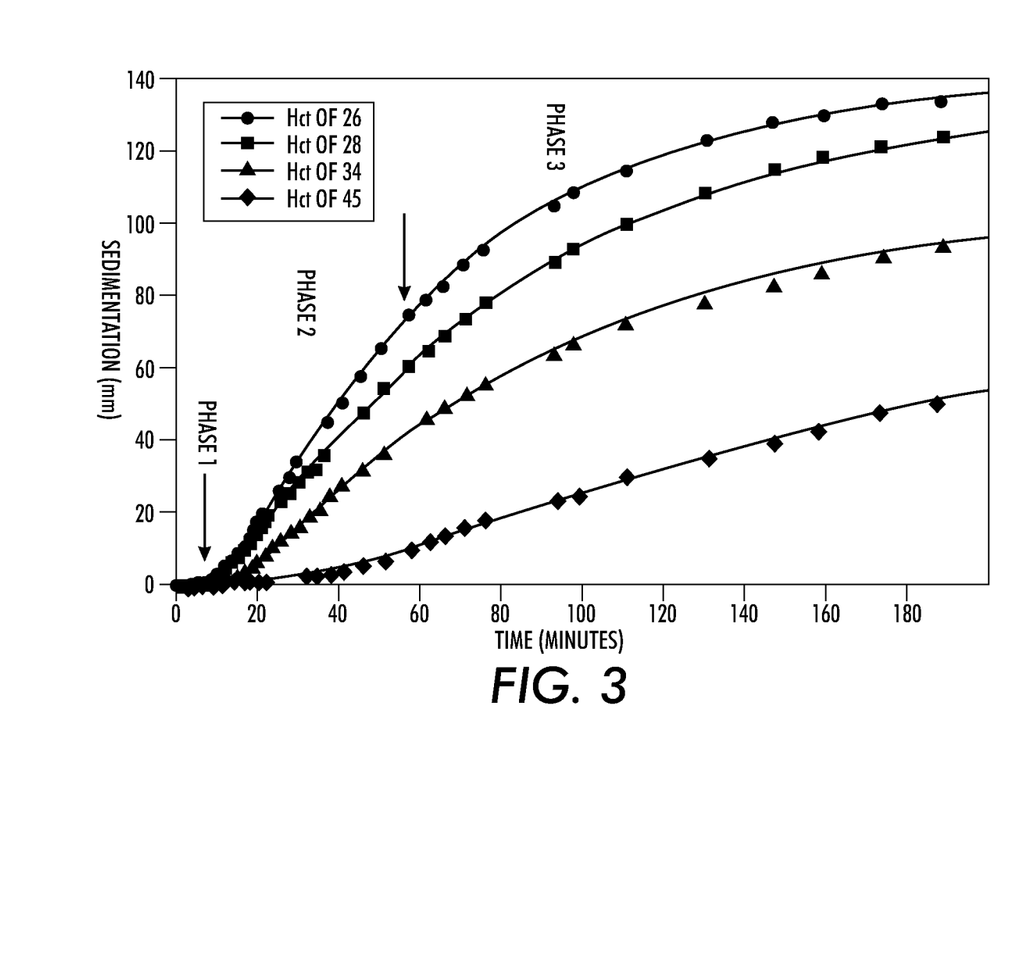
FIG. 3 is a chart illustrating sedimentation rate of red blood cells as a function of time.

It is known that red blood cells, by volume, make up a large portion of blood. For instance the hematocrit (Ht or HCT) or packed cell volume (PCV) or erythrocyte volume fraction (EVF) is the proportion of whole blood volume that is occupied by red blood cells. It is normally about 48% for men and 38% for women. It is also known that in unstirred blood that has been treated with an anti-clotting agent (e.g., sodium citrate K$_3$EDTA, etc.) red blood cells will nucleate into stable spherical aggregates that settle out over time. The radius of the aggregated spheres will depend upon the suspending medium and the hematocrit. Red blood cell suspensions undergo sedimentation only after aggregates are formed. Aggregation is a two-step process: First, red blood cells associate in long chains (i.e., rouleaux formation). Next, these chains form spheres of uniform size. The requirements for this well-defined process are an electrolyte and a neutral or negatively charged macromolecule in the solution and a metabolically active red cell. Red blood cell sedimentation follows an S-shaped curve with time (see FIG. 3):

i. There is a delay in the start of sedimentation; during this time the rate of sedimentation is zero (phase 1 of the curve).

ii. The next segment (phase 2) is linear: sedimentation continues at a constant rate.

iii. Finally (phase 3) the rate levels off to zero: sedimentation is completed.

As can be seen from FIG. 3, blood with lower HCT values settles faster, as they form larger aggregates quicker than blood with higher HCT values. The rouleaux formation is driven by the presence of certain macromolecules (e.g., polymers like dextran, fibrinogen, etc.), which bind to receptor sites on the red blood cells. The concentration of these macromolecules determines how large the aggregates can grow and, hence, how fast they settle. Platelets and the white blood cells do not have receptor sites for the macromolecules, but rather stay in solution and concentrate in the blood plasma phase of the blood. Rouleaux (singular is rouleau) are stacks of red blood cells which form because of the unique discoid shape of the cells in vertebrate body. The flat surface of the discoid red blood cells give them a large surface area to make contact and stick to each other; thus, forming a rouleau.

While the mentioned delay time (Phase 1) will vary depending on a number of factors, a rough approximation of Phase 1 is between 5 to 10 minutes, with further sedimentation (Phase 2) taking hours to overnight or more. Therefore it is understood that a blood separation and extraction device and procedure which employs sedimentation would desirably look to decrease this delay time and sedimentation time.

In this regard, a useful concept or phenomenon is that under appropriate conditions blood moving in a channel causes red blood cells within the blood to align with each other in the channel direction. Therefore in one embodiment of the present application and as illustrated by a blood separation device 400 of FIG. 4, aggregation arrangement 102, 202 of FIGS. 1 and 2, is implemented to include a curved microfluidic particle manipulation device 402, such as in the form of a spiral channel, used to induce an alignment and chaining effect (rouleaux formation) of the red blood cells. Therefore instead of simply waiting for the red blood cells to aggregate on their own, in this design, blood 404 is provided with a polymer 406 and is passed through curved microfluidic particle manipulation device 402 to actively assist in speeding up red blood cell alignment and chaining. It is understood the polymer 406 is added to the blood either prior to, during or after the blood has been delivered to curved microfluidic particle manipulation device 402.

Figure 4:
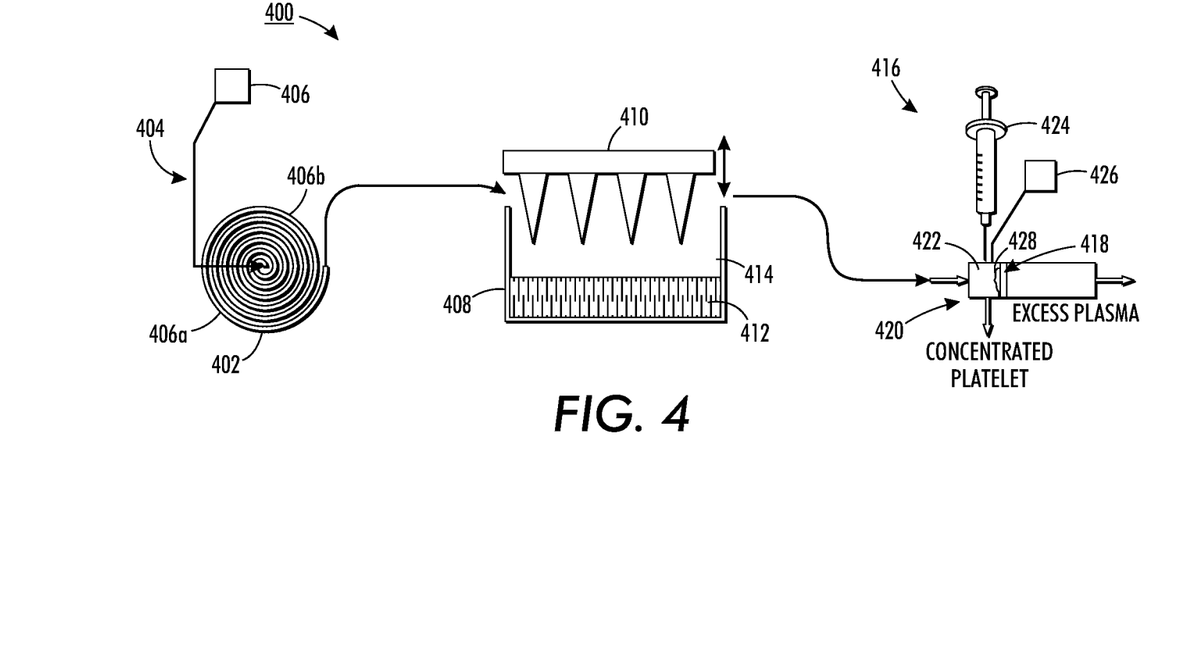
FIG. 4 illustrates a more detailed view of a blood separation device according to the present application.

The curved microfluidic particle manipulation device 402 is used to assist in the formation of the rouleaux, where the blood flow in the channel acts to align the individual red blood cells in chained strings to form the precursor of the rouleaux. The spiral channel of device 402 is one embodiment of such a channel configuration and is understood that other curved channels may also assist in such alignment. The elasticity and deformability of the red blood cells allows red blood cells to remain intact as blood flows through the narrow spiral channels. Specific control parameters to obtain the noted alignment include the volume fraction of the red blood cells (i.e., the hematocrit, Ht), the channel cross-sectional area, and the flow velocity.

Output (i.e., blood with aligned chained red blood cells) from device 402 is then delivered to a sedimentation tank 408 and an extraction device 410, such as a syringe array (these elements being an embodiment of red blood cell separation arrangement 106, 206 of FIGS. 1 and 2). The blood is maintained in sedimentation tank 408 to allow aggregation of red blood cells 412. This increases the density of the aggregated red blood cells causing movement to the bottom of sedimentation tank 408 and separation from the platelets and white blood cells in blood plasma 414 which moves toward the surface of sedimentation tank 408.

Alignment and chaining of red blood cells by device 402 acts to increase the speed of sedimentation, another step which further increases the speed of sedimentation is accomplished by providing a particular configuration of sedimentation tank 408. More specifically sedimentation speed can be increased by appropriate reduction in the height or distance provided for sedimentation, i.e., the sedimentation height of tank 408. Therefore, in FIG. 4, sedimentation tank 408 is designed to be wider and longer than it is deep by a ratio of 10:1 to 100:1, where the larger values (i.e., 10 and 100) refer respectively to the width and length of the container and the smaller number (i.e., 1) refers to the height of the container. It is of course understood that other ratios may also be acceptable and the above is simply one example.

As understood, sedimentation speed has a non-linear behavior, i.e., the denser the red-blood cell phase becomes, the smaller/slower the sedimentation speed. By understanding this characteristic an optimum relationship between sedimentation height and sedimentation time for extracting a fixed volume of substantially red blood cell-free blood plasma may be determined for a particular implementation. The optimal operation may include either single-pass or multiple passes of the blood through the sedimentation process. These are issues to consider when designing operating specifications such as process time and so forth.

Additional actions to speed up red blood cell alignment as well as the speed of sedimentation include diluting the blood (a factor of 2 can reduce the aggregate formation time by a factor of 2 while doubling the sedimentation speed—see FIG. 3) and/or by adding more of the macromolecules (e.g., polymer) that induces the rouleau formation. In one embodiment the dilution of the blood is accomplished by using a benign buffer solution that does not add to regulatory requirements. The diluted effluent (blood and diluting substance) can be re-concentrated by subsequent operations.

Once the red blood cells have settled sufficiently (e.g., a known appropriate time period has passed) an extraction arrangement 410 is used to remove the platelet-rich blood plasma that has been separated from the red blood cells. To avoid stirring up the settled red blood cells, the extraction arrangement 410 of FIG. 4 is embodied as a group of movable syringes (e.g., an array). The individual syringes are positioned at different locations near an upper surface of the sedimentation tank to withdraw the platelet rich blood plasma, which has been separated from the red blood cells. This extraction array is employed rather than a single syringe tip in order to minimize horizontal cross-flow above the sediment (red blood cell) layer 412. This extraction may be manually or automatically accomplished in a known manner, where the tips of the syringes are moved into the plasma for extraction.

The obtained platelet rich blood plasma 414 is then provided to a concentration system 416 (which illustrates one embodiment of the concentration arrangement 108, 208 shown in FIGS. 1 and 2). Concentration system 416 of FIG. 4 includes a filter membrane 418, located in a channel or other appropriate fluid container 420, wherein the filter in one embodiment is arranged in a dead-end configuration. The filter 418 is positioned in the channel 420 to receive plasma that has been separated from the red blood cells. Filter 418 is sized to block platelets in the plasma and to pass the plasma and components therein that are smaller than the platelets. In this embodiment with a typical platelet diameter being about 3 um, a filter with 1 um pore size is sufficient to block transmission of the platelets, while allowing the other portions to flow through. The described arrangement collects a concentrated platelet sample 422. Then an extraction device (e.g., a plunger or syringe) 424 is provided on the blocking side of filter 418 and is used to collect the concentrated platelet sample 422 by either pushing out or picking up the concentrated platelet sample.

To avoid lysing of the platelets, it is desirable to minimize cross-membrane pressure. Thus in one embodiment concentration system 416 is designed to include a cross-flow arrangement 426 positioned to deliver a flow of fluid 428 at the surface of filter 418 that is tangential to the flow of the platelet rich plasma 414, wherein the flow of fluid being concentrated is flowing towards filter 418.

In still another embodiment instead of a dead end design, where the plasma is made to flow directly at filter 418, a cross flow design is used where the plasma flow is generally tangential to the filter surface and through gravity and density plasma and components in the plasma pass though the filter.

Figure 5:
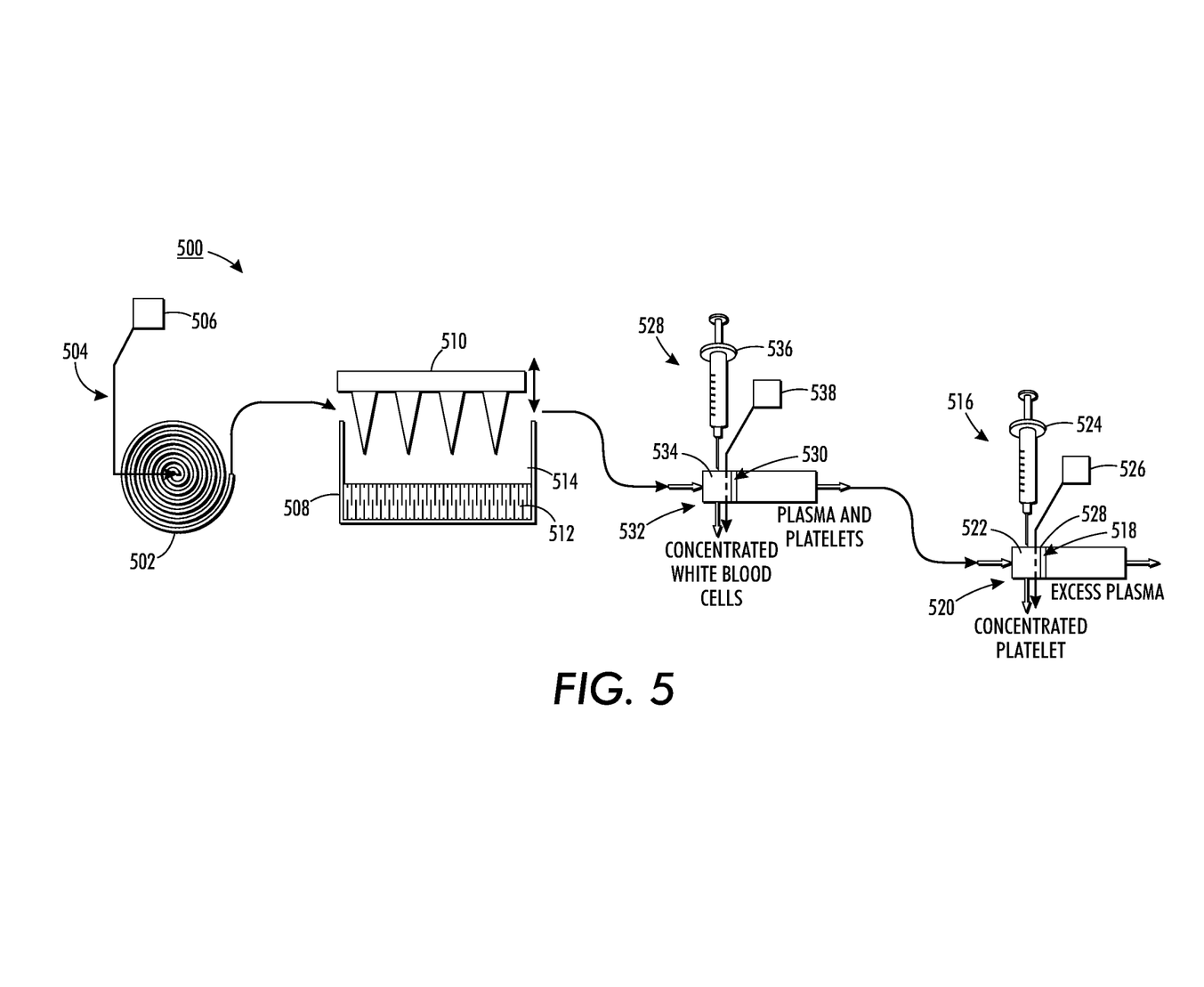
FIG. 5 illustrates a more detailed view of an alternative embodiment for a blood separation device according to the present application.

Turning to FIG. 5, depicted is an alternative blood separation device 500. This device is similar to that shown in connection with FIG. 4, including an optional curved microfluidic particle manipulation device 502, configured to receive blood 504 which has or will be provided with a polymer 506, a sedimentation tank 508 and an extraction array 510. The blood is maintained in sedimentation tank 508 to allow aggregated red blood cells 512 to separate from blood plasma 514. The system also includes, similar to FIG. 4, a platelet concentration system 516, which uses an appropriate sized filter membrane 518, in a channel 520, capable of holding a concentrated platelet sample 522, along with a plunger or syringe 524 and a cross-flow arrangement 526. However, in addition to these elements, blood separation device 500 further includes a white blood cell separator system 528, which in this embodiment is configured to include an appropriately sized filter 530, located within a channel or other appropriate fluid container 532, where the filter is sized to filter out white blood cells into a concentrated white blood cell sample 534 while allowing the remainder of the blood plasma and the smaller platelets to pass. The blood plasma including platelets is subsequently handled by platelet concentration system 516. White blood cell separator configuration 528 also includes a collection mechanism 536 in the form of a plunger/syringe or other appropriate collection device or arrangement. Also provided is a cross flow arrangement 538, similar to cross-flow arrangement 526. Still further, rather than a dead end arrangement in other embodiment a cross-flow arrangement may be employed. It is understood the filters used for white blood cell concentration will have a cutoff size between platelet and white blood cells, which generally have sizes from 8 to 20 um.

Figure 6:
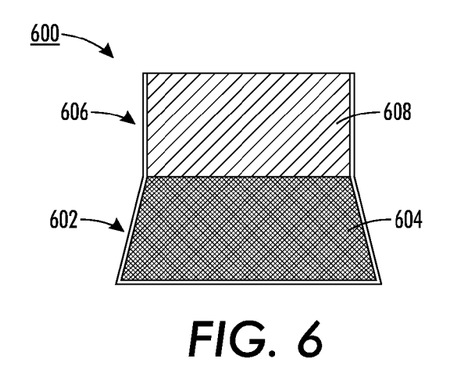
FIG. 6 depicts an alternative sedimentation tank for use in a blood separation device according to the present application.

Turning to FIG. 6, an alternative to the sedimentation tank shown in FIGS. 4 and 5 is disclosed. Particularly sedimentation tank 600 is designed such that a lower portion 602 is made in a hexagonal or other design which results in a larger volume for the red blood cell aggregations 604, whereas an upper portion 606 is narrower to have greater depth but less volume. This design is intended to still allow for an increased speed of sedimentation as lower portion 602 would not need to be as deep (to hold the same volume) if the lower portion 602 were the same design as the upper portion 606. By increasing the depth of the upper portion 606 a thicker layer of the blood plasma 608 is collected, minimizing agitation of the red blood cell 604 layer during platelet retrieval. As is clear, in this disclosure the sedimentation tanks are not to be considered test tubes.

Figure 7:
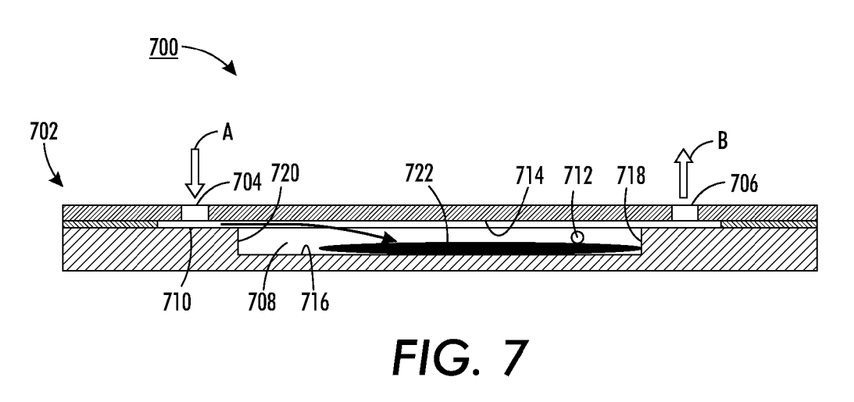
FIG. 7 It depicts a dynamic sedimentation system or cell used in a blood separation system according to the present application.

FIG. 7 shows an alternative sedimentation embodiment in the form of a dynamic sedimentation system or cell 700, which permits for a continuous flow separation system based on field flow fractionation (FFF). Cell 700 comprises a body 702 defining an inlet 704, an outlet 706, and an interior hollow region or expansion cavity 708 generally extending there between. It is preferred that the inlet 704 includes an angled region or bend (e.g., a 90 degree bend), such as bend 710. The 90 degree or angled bend 710 at the inlet is utilized to defuse and slow down an incoming flow to result in a more laminar flow field over the expansion cavity 708. The recessed design of cavity 708 acts to trap particles, especially in the vortex or re-circulation area created at the bottom right corner of the flow cell thus keeping the particles tightly focused.

The cell body 702 also defines a sample discharge port 712. The expansion cavity 708 is defined between an upper wall 714, and a lower wall 716. The cell 700 also comprises a collection wall 718 generally extending at right angles with respect to flow within the cell. Defined at an opposite end of the region from the collection wall 718, is an inlet wall 720.

With continuing reference to FIG. 7, as a flow stream containing red blood cells which are to be separated from plasma enters the cell 700 through the inlet 704 as shown by arrow A, the bend 710 within or proximate the inlet 704 serves to promote laminar flow once the flow stream enters the expansion chamber or cavity 708 and the velocity of the stream decreases. This reduction in flow speed allows the aggregating aligned and chained red blood cells 722, which are the heaviest portion of blood, to drop to the bottom surface or lower wall 716 and accumulate. These red blood cells 722 may be removed via discharge port 712. The less dense components of the blood (e.g., the red blood cell depleted plasma having platelets and/or white blood cells) exit the dynamic sedimentation cell 700 through outlet 706 as shown by arrow B.

In one embodiment cell 700 may have the following dimensions: channel width 10 cm; channel height 0.05 cm; channel length 10.0 cm; cavity height 0.10 cm flow cross-section 0.50 cm$^2$; channel volume 5.00 mL; and cavity volume 10 mL. Having a cell with these characteristics in one implementation the blood is provided at a flow rate of 4.1666668E-02 mL/s, resulting in a flow velocity of 8.3333336E-02 cm/s in the channel and a cavity flow velocity of 2.7777778E-02 cm/s. Then in Y-tracking, sedimentation velocity is 9.7222225E-04 cm/s, with a time to deposition of 154.2857 seconds, and X-tracking has a deposition distance of 4.285714 cm. Deposition being understood to be where the transported particles fall out of the transporting medium and settle on a surface. It is further mentioned that the y-direction refers to the height (or sedimentation) direction, and the x-direction refers to the left-to-right direction corresponding to the main flow direction. The overall process time is 1200 s (20 minutes), with a detention time of 360 seconds (s) (6 minutes). Where a detention time is the time the fluid is within the cell.

In an alternative embodiment cell 700 may be configured such that a small bias voltage is applied to the cell which acts to push the red blood cells towards the bottom of the flow cell (i.e., red blood cells are negatively charged).

Figure 8:
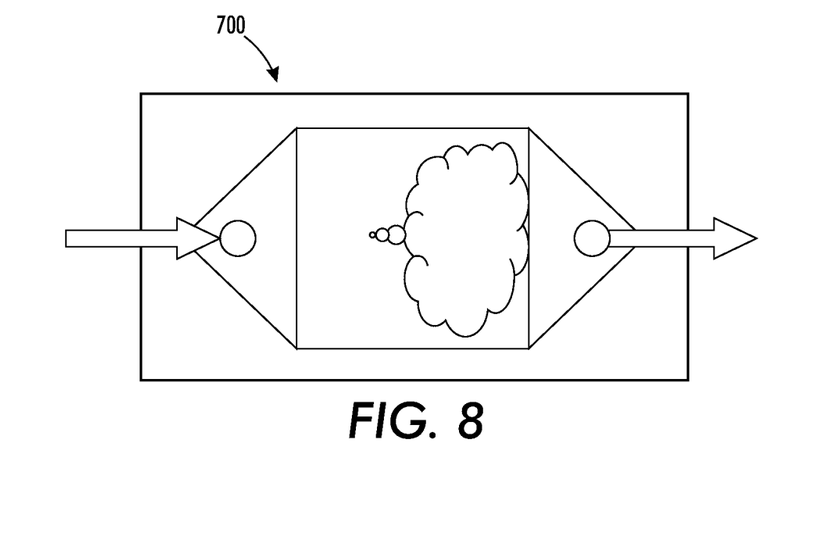
FIG. 8 is a top view of FIG. 7.
Figure 9:
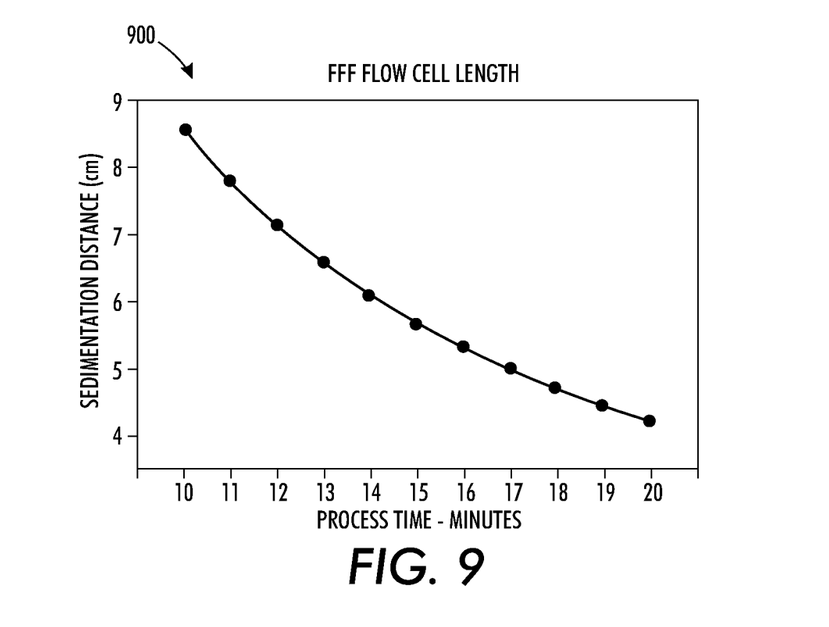
FIG. 9 is a chart showing process time (minutes) versus sedimentation distance (cm) for the flow cell of FIG. 7.

Turning to FIG. 8 depicted is a top view of the dynamic sedimentation device 700 FIG. 7. FIG. 9 is a chart 900 showing process times (minutes) versus sedimentation distance (cm) for the flow cell 700 of FIGS. 7 and 8.

Challenges with a continuous flow separation system design is the large amount of red blood cells within the blood, this may require a large volume of red blood cells in the expansion chamber 704 and the constant cross-flow over the sedimentation layer, which may keep a small amount of red blood cells in solution. To address this issue and as shown in FIG. 10, cell 1000 having a body 1002, inlet 1004 and 1006 is constructed with an enlarged expansion chamber 1008 compared to the dimensions of expansion chamber 708 of FIG. 7.

Figure 10:
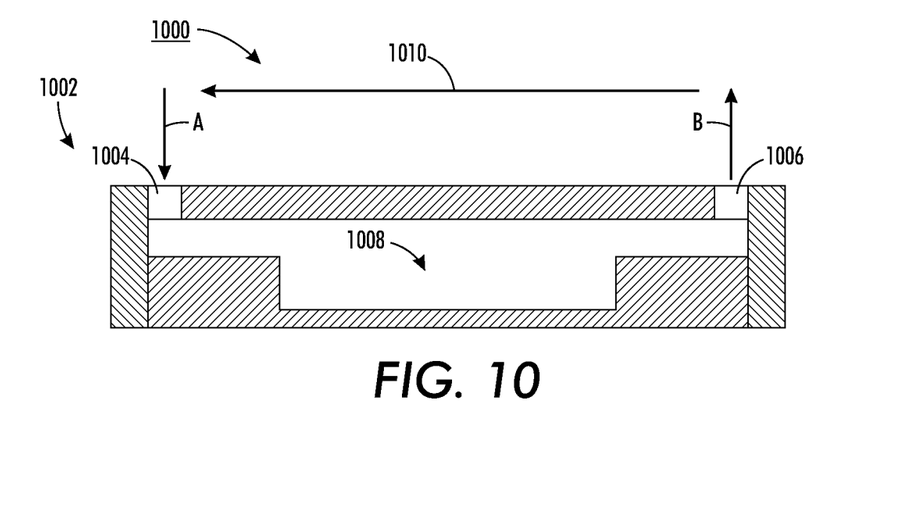
FIG. 10 shows an alternative dynamic sedimentation system or cell according to the concepts of the present application.

It is to be appreciated in both the embodiments of FIGS. 7 and 10 the process may be designed to allow the red blood cell depleted blood plasma to recirculate through cells 700 or 1000 to separate additional amounts of red blood cells from the remaining blood plasma. For example this is shown by line 1010, which shows out fluid (arrow B) being resupplied to inlet 1004 (e.g., arrow A). Additionally, repeated separation operations can be accomplished by employing two or more dynamic cells (700 and/or 1000) in series such that the output of one cell feeds into a next cell.

Figure 11:
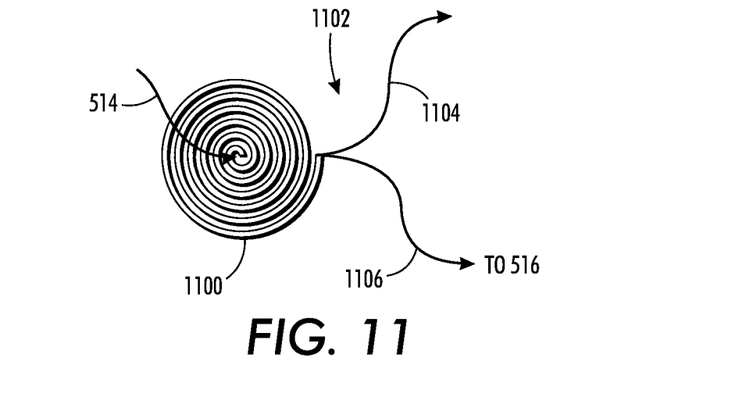
FIG. 11 depicts an alternative white blood cell separator arrangement.

Turning to FIG. 11, in an alternative embodiment, the white blood cell separator 528 of FIG. 5 may be implemented by a curved micro separation device 1100, which in one embodiment is in the form of a spiral design. In this embodiment, the blood plasma from which red blood cells have been separated is provided to an input of device 1100. By designing device 1100 to apply hydrodynamic forces which separate or otherwise move particles based on sizes, the white blood cells are separated from at least a portion of differently sized platelets. The device 1100 further includes a divided output 1102, with one outlet line 1104 carrying white blood cells and another outlet line 1106 carrying platelets in the plasma. As the platelets may be fairly evenly distributed in the plasma and therefore within the stream of the concentrated white blood cells, multiple passes through device 1100 may provide a more successful separation of the white blood cells from the platelets. Additionally, two or more of devices 1100 may be used in series to obtain improved separation where an output of one device 1100 is fed to an input of a second or following device 1100.

It is appreciated that in addition to the spiral configuration used within this application, including the use of the spiral mechanisms in FIGS. 4, 5 and 11 other curved configurations (e.g., s-curves) may also be used. Also, while curved and/or spirals devices using hydrodynamic forces are employed to provide the alignment of red blood cells, other mechanisms and associated methods to induce alignment and chaining include ultrasonic focusing and AC electrical perturbation.

It is to be understood that aspects of the present concepts may be used in a variety of combinations. For example, various embodiments of the red blood cell alignment and aggregation arrangement, the red blood cell separation arrangement, the concentration arrangement, the collection arrangement, and the white blood cell concentration arrangement may be used in different combinations of each other, as well as in combination with known separation processes.

The blood separation devices described above may be designed as portable and/or disposable devices. Various operations such as the extraction of the plasma and/or the extraction of the concentrated platelets may be fully mechanized or accomplished by operator action.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A system for extraction of platelets from blood comprising:
   an aggregation arrangement configured to aggregate red blood cells suspended in the blood, wherein the aggregation arrangement includes a curved microfluidic particle manipulation device, configured to align red blood cells within the blood;
   a separation arrangement configured to separate the aggregated red blood cells out of the blood, wherein the platelets and red blood cells are separated from each other, wherein the separation arrangement includes a sedimentation system and wherein the separation arrangement further includes an extraction or outlet arrangement positioned on an upper surface of the sedimentation system to withdraw plasma which has been separated from the red blood cells, the plasma having platelets contained therein; and
   a platelet concentration arrangement positioned to receive the plasma having platelets from the separation arrangement and configured to concentrate the received platelets.

2. The system of claim 1, wherein the sedimentation system is a static sedimentation system having a sedimentation tank that is wider and longer than it is deep.

3. The system of claim 2, wherein the extraction arrangement further includes an array of extraction devices positioned at different locations at the upper surface of the sedimentation tank.

4. The system of claim 1, wherein the sedimentation system is a static sedimentation system having a sedimentation tank that is wider at its bottom than at its top.

5. The system of claim 1, wherein the sedimentation system is a dynamic sedimentation system in the form of a flow cell arrangement, wherein the flow cell arrangement includes a fractionation configuration and the outlet arrangement.

6. The system of claim 1, wherein the platelet concentration arrangement includes a filter positioned to receive plasma that has been separated from the red blood cells, the filter sized to block platelets in the plasma and to pass portions of the plasma that are smaller than the platelets.

7. The system of claim 6, further including a cross-flow arrangement positioned to deliver a flow of fluid that is tangential to a flow of fluid being concentrated, wherein the flow of fluid being concentrated is flowing towards the filter.

8. The system according to claim 6, further including a platelet extraction arrangement for removal of the concentrated platelets.

9. The system of claim 1, further including a white blood cell separation arrangement for separating out the white blood cells from the plasma separated from the red blood cells.

10. The system of claim 9, wherein the white blood cell separation arrangement is a second filter sized to block passage of the white blood cells but allow the platelets to pass.

11. The system of claim 9, wherein the white blood cell separation arrangement separator is formed as a second curved microfluidic particle manipulation device configured to consolidate the white blood cells for removal from at least some of the platelets.

12. A method for extraction of platelets from blood:
   aligning and chaining together red blood cells suspended in the blood by passing the blood through a curved channel;
   aggregating the aligned and chained red blood cells;
   separating the aggregated red blood cells, in a separation arrangement when the aggregation of the red blood cells causes the aggregated red blood cells to separate from platelets in the blood, wherein the separation arrangement includes a sedimentation system, and wherein the separation arrangement further includes an extraction or outlet arrangement positioned to withdraw plasma which has been separated from the red blood cells, the plasma having platelets contained therein; and
   concentrating the platelets that have been separated from the red blood cells by use of a platelet concentration arrangement positioned to receive the platelets from the separation arrangement.

13. The method according to claim 12 wherein the passing the blood through a curved channel includes passing the blood through a spiral channel.

14. The method according to claim 12 wherein the sedimentation system includes performing static sedimentation operations on the blood.

15. The method according to claim 12 wherein the sedimentation system includes performing dynamic sedimentation operations on the blood.

16. The system according to claim 1 wherein the curved microfluidic particle manipulation device is a spiral microfluidic particle manipulation device.

17. The system according to claim 11 wherein the second curved microfluidic particle manipulation device is a second spiral microfluidic particle manipulation device.

* * * * *